United States Patent

Sawai et al.

Patent Number: 5,166,388
Date of Patent: Nov. 24, 1992

[54] STABILIZED COMPOSITION OF PHYTIC ACID

[75] Inventors: Kiichi Sawai, Funabashi; Masayasu Kurono, Mie; Hiromoto Asai, Nagoya; Takahiko Mitani, Mie; Naohisa Ninomiya, Nagoya, all of Japan

[73] Assignee: Sanwa Kagaku Kenkyusho Co., Ltd., Nagoya, Japan

[21] Appl. No.: 549,048

[22] Filed: Jul. 6, 1990

[30] Foreign Application Priority Data

Jul. 14, 1989 [JP] Japan .................... 1-181686

[51] Int. Cl.$^5$ .......................... A61K 7/32; C07F 9/02
[52] U.S. Cl. ........................ 558/161; 424/65
[58] Field of Search .......... 260/413, 422; 558/160, 558/161; 536/117

[56] References Cited

U.S. PATENT DOCUMENTS 4,477,386 11/1984 Fujita ..................... 260/412.2

OTHER PUBLICATIONS

Chemical Abstracts. 1968, vol. 71, 105207.
Chemical Abstracts, 1981, vol. 95, 167441t.
Chemical Abstracts, 1970, vol. 73, 4160g.
Chemical Abstracts, 1973, vol. 79, 19035t.
Chemical Abstracts, 1986, vol. 105, 21316j.

*Primary Examiner*—Dale R. Ore
*Attorney, Agent, or Firm*—Armstrong & Kubovcik

[57] ABSTRACT

A stabilized composition of phytic acid is obtained by the steps of:
  heating and drying rice bran de-fatted by pressing;
  adding acidic water of pH 3 to 5 to the dried rice bran, stirring the solution and completing the stirring before the pH of the solution reaches 5.7; and
  heating the thus obtained liquid extract to solidify protein components, followed by the removal of the solid matters by filtration. This composition is advantageously used for removing uraroma and body odor.

1 Claim, No Drawings

STABILIZED COMPOSITION OF PHYTIC ACID

BACKGROUND OF THE INVENTION

1. Field of the Invention

The present invention relates to a stabilized composition of phytic acid and, more particularly, to a stabilized composition of phytic acid obtained by extracting degreased or de-fatted rice bran from water in an acidic region of pH 5.7 or less as well as its use as oral or body odor removers.

2. Prior Art

Phytic acid, a hexaphosphate of inositol, occurs naturally as a mixed salt (phytin) with calcium, magnesium and potassium and are relatively abundantly found in the rinds of fruit plants, etc.

Phytic acid and its salts are now used as pharmaceuticals. For instance, calcium phytate is used as a calcium enricher, sodium phytate for the prevention of relapse of calculosis, and potassium phytate for the treatment of hypercalcemia.

Phytic acid is also used as food additives, for preventing the occurrence of strabite in canned foods or the blackening of canned foods, for preventing the discoloration of fruits and drinking water, for promoting fermentation, for preventing the oxidation of edible oil and for other purposes.

Further, the inventors have found that phytic acid is effective not only against removing body odor and uraroma but also for detoxication (Japanese Patent Application Nos. 63 (1988)-19946 and -116338 specifications).

A problem with phytic acid, however, is that it is so lacking in storage stability that it should be preserved in a refrigerator or cold, dark place of 10 or less, since it turns from pale yellow into brown upon permitted to stand for an extended period of time and is colored by heating.

Another problem with phytic acid is that when powderized so as to improve storage stability, it suffers from polymerization at the powderizing step, its own hue changes to deep blue, and its viscosity increases.

SUMMARY OF THE INVENTION

Making efforts for the purpose of stabilizing phytic acid and maintaining its action and effect, the inventors have now found that commercially available phytic acid products vary in pharmacological action from lot to lot, and that a phytic acid-containing composition obtained by extracting de-fatted rice bran from water in an acidic region of pH 3 to 5 makes a contribution to stabilizing phytic acid.

It is therefore an object of the present invention to provide a stabilized phytic acid which is obtained by the steps of heating and drying rice bran de-fatted by pressing; adding acidic water of pH 3 to 5 to the dried rice bran, stirring the solution and completing the stirring before the pH of the solution reaches 5.7; and heating the thus obtained liquid extract to solidify protein components, followed by the removal of the solid matters by filtration.

At a pH of 5.7 or higher, phytin precipitates.

DETAILED DESCRIPTION OF THE INVENTION

Typical results of analysis of the composition according to the present invention are summarized in Table 1.

TABLE 1

| What was analyzed | Results | Note | Methods for analysis |
|---|---|---|---|
| Water content | 95.1% | | Drying by heating under reduced pressure |
| Protein | 0.6% | 1 | Kjeldahl method |
| Fat | 0 | | Soxhlet extraction |
| Ash content | 1.1% | | Direct ashing |
| Carbohydrates | 3.2% | 2 | |
| pH | 4.9 | | Glass electrode method |
| Insoluble matter content | <0./1% | 3 | |
| Phosphorus | 308 mg/100 g | | Vanadomolybdate absorbance method |
| Phytic acid as meso-inosite hexaphosphate | 1.06% | | Vanadomolybdate absorbance method |

Note 1: a conversion factor of nitrogen/protein: 6.25
Note 2: 100 - (water content + protein + lipid + ash content)
Note 3: an amount of residues of a sample under test after filtration through Filter Pater No. 5A made by Toyo.

It is noted that the stabilized composition according to the present invention may advantageously be used either in liquid form or in powdery form obtained by spray drying, etc.

It is also understood that even when the composition according to the present invention is used independent of phytic acid, it produces as much effect and action as phytic acid.

EXAMPLES

The present invention will now be explained specifically but not exclusively with reference to the following examples.

EXAMPLE 1

Oily components such as germ oils, oryzanol and ferula esters were squeezed out of rice bran by pressing to obtain a pressed matter, which was then dried by heating. The thus dried product was used as an input material.

Added to 1 kg of the input material (on dry basis) were 5000 cc of water to obtain an aqueous solution, which was then regulated to pH 5 with liquid phytic acid. Under agitation at room temperature, small portions of liquid phytic acid were added to the solution while taking care such that there was no sharp rise in pH. Before a pH of 5.7 was reached, stirring was stopped (after about 3 hours). After the removal of solids and insoluble matters by pressing, the crude liquid extract was boiled to solidify protein, which was then filtered out at 300 mesh to obtain 540 ml of a liquid extract. One hundred (100) ml of the liquid extract contained about 1 g of compounds based on inositol phosphate.

The above-mentioned operations should always be carried out at a pH of 5.7 or lower. At higher than pH 5.7, phytin precipitates.

Added to and mixed with 500 ml of the liquid extract were 20 g of cyclodextrin and 3 g of dextrin, and the mixture was spray-dried at 155 to obtain about 45 g of powders.

The powders are directly usable as pharmaceuticals, stabilizers for phytic acid preparations, nutrient enrichers for foodstuffs, taste enrichers for salted vegetables and so on.

EXAMPLE 2—TABLET

| Composition of Ex. 1 (about 2000 mg, calculated as a compound based on inositol phosphate) | 2000 mg |
|---|---|
| Corn starch | 190 mg |
| Crystalline cellulose | 300 mg |
| Magnesium stearate | 10 mg |

Predetermined amounts of the above ingredients were uniformly mixed together and compressed into a tablet of 16 mm in diameter and weighing 2500 mg.

EXAMPLE 3—CAPSULE

| Composition of Ex. 1 (about 20 mg, calculated as a compound based on inositol phosphate) | 200 mg |
|---|---|
| Lactose | 20 mg |
| Corn starch | 38 mg |
| Magnesium stearate | 2 mg |

Given amounts of the above ingredients were uniformly mixed together and packed in a No. 2 capsule.

STABILIZATION TEST EXAMPLE 1

For the stability of an aqueous solution of phytic acid and phytic acid per se under severe conditions, an amount (% by weight) of the composition obtained in Ex. 1 was added to varied amounts of commercially available phytic acid to prepare liquids under test to investigate an effect upon stabilizing phytic acid. The results, shown in Table 2, have revealed that the composition of the present invention has a much increased effect upon preventing decomposition and discoloration.

TABLE 2

Amount of phytic acid remaining after stability testing in % by weight

| Sample | Container | Day 0 | After 3 weeks at 60 |
|---|---|---|---|
| Liquid A | Glass bottle | 100.2 | 98.2 |
| Liquid B | Glass bottle | 100.1 | 97.8 |
| Control a | Glass bottle | 97.9 | 69.1 |
| Control b | Glass bottle | 97.7 | 68.5 |
| Control c | Glass bottle | 100.8 | 61.0 |

Liquid A: 20% aqueous solution of phytic acid obtained by the addition of commercially available phytic acid to the composition of the present invention.
Liquid B: 40% aqueous solution of phytic acid obtained by the addition of commercially available phytic acid to the composition of the present invention.
Control a: 20% aqueous solution of commercially available phytic acid.
Control b: 40% aqueous solution of commercially available phytic acid.
Control c: Commercially available phytic acid powders.

TEST EXAMPLE 2—REMOVAL OF ODOR

For experimentation, pre-fed Afghan long-haired dogs, three for each group, confirmed to be normal by general physical examination, were used. A test group of animals was fed under normal conditions with feed containing the spraydried powders of Ex. 1 in an amount of 1 g per 1 kg of weight once a day over one week.

By permitting a total of three inspectors make an inspection of the sebum smells (doggy smells) of the back and maned regions of the animals, smelling tests were carried out, in which it was judged to be significant when, of the three inspectors, two found a significant difference between the test and control groups. As a result, all the inspectors concluded that the sebum smells (doggy smells) were completely or considerably removed from all the animals belonging to the test group; this means that the present composition is effective against removing body odor.

TEST EXAMPLE 3—IN VITRO TESTING ON REMOVING ORAL ODOR

1) Samples i. Physiological Oral Odor (Artificial Oral Odor)

Use was made of 5 ml of a solution containing in absolute quantity 10 g of methyl mercaptan, 250 g of hydrogen sulfide and 100 g of dimethyl sulfite.

ii. Smelling of Garlic

Use was made of a fresh, grated garlic (S & B Shokuhin Co., Ltd.).

iii. Smelling of Gyoza—A Fried Dumpling Stuffed With Minced Pork

Use was made of one portion of commercially available gyoza (eight pieces).

2) Testing Procedures

The tablet of the present invention in powdery form was added to 100 ml of each sample dissolved in water, and the solution was packed in a 2-liter sample bag, in which it was permitted to stand at 40 for 15 minutes. Measurement was made with a detecting tube.

As control, use was made of a sample to which 1500 mg of cyclodextrin were added in place of the tablet.

3) Test Results

The results are summarized in Tables 3-6, in which the "residual ratio" is defined with respect to the control concentration being 100%.

TABLE 3

Man-made oral malodor (Methyl mercaptan detector)

| | Conc. | Residual Rate | Amount of odor trapped per 2 tablets |
|---|---|---|---|
| Control | 6.5 ppm | — | — |
| 60 tablets | 5.0 ppm | 76.9% | 0.19 g |
| 30 tablets | 5.5 ppm | 84.6% | 0.26 g |
| 15 tablets | 5.9 ppm | 90.8% | 0.46 g |
| 2 tablets | 6.3 ppm | 96.9% | 0.77 g |

TABLE 4

Man-made maloral odor (Hydrogen sulfide detector)

| | Conc. | Residual Rate | Amount of odor trapped per 2 tablets |
|---|---|---|---|
| Control | 5.8 ppm | — | — |
| 60 tablets | 3.5 ppm | 60.3% | 0.21 g |
| 30 tablets | 3.9 ppm | 67.2% | 0.35 g |
| 15 tablets | 4.8 ppm | 82.8% | 0.54 g |
| 2 tablets | 5.4 ppm | 93.1% | 1.09 g |

TABLE 5

Smelling of garlic (Methyl mercaptan detector)

| | Conc. | Residual Rate | Amount of odor trapped per 2 tablets |
|---|---|---|---|
| Control | 6.0 ppm | — | — |
| 60 tablets | 1.2 ppm | 20.0% | 0.61 g |
| 30 tablets | 2.0 ppm | 33.3% | 1.02 g |
| 15 tablets | 3.5 ppm | 58.0% | 1.92 g |

TABLE 5-continued

Smelling of garlic (Methyl mercaptan detector)

|  | Conc. | Residual Rate | Amount of odor trapped per 2 tablets |
|---|---|---|---|
| 2 tablets | 5.0 ppm | 83.3% | 3.83 g |

TABLE 6

Smelling of gyoza (Methyl mercaptan detector)

|  | Conc. | Residual Rate | Amount of odor trapped per 2 tablets |
|---|---|---|---|
| Control | 15.0 ppm | — | — |
| 60 tablets | 6.0 ppm | 40.0% | 1.15 g |
| 30 tablets | 9.8 ppm | 66.3% | 1.33 g |
| 15 tablets | 13.5 ppm | 90.0% | 1.15 g |
| 2 tablets | 14.2 ppm | 94.7% | 3.07 g |

4) Consideration

For measurement with an in vitro detector, the malodorants were used in large excess relative to the actual dosage of the present tablets, taking measuring sensitivity into account.

The use of from two (one dose) up to sixty (thirty doses) tablets of the present invention was found to be effective against reducing the malodorants noticeably.

By calculation, it has thus been noted that the amount of the malodorant trapped per dose of the present tablets is 0.77 g to 3.83 g/2 tablets. In this connection, those who have a foul breath are said to emit about 0.5 g of methyl mercaptan per several hours. That amount of methyl mercaptan can all be virtually trapped by a single dose of the present tablets, and the smaller the dose of the tablets used, the more the amount of the malodorant trapped per dose.

As mentioned above, the tablets of the present invention can produce an effect upon removing as much offensive a smell as about 0.5 g of methyl mercaptan.

TEST EXAMPLE 4—IN VIVO ORAL ODOR REMOVING TEST

I) Organoleptic Testing on the Odor of Gyoza

1) Testing Procedures

Immediately after having a subject eaten one portion of gyoza, 3 liters of breaths were gathered in a testing bag (made by Gaskuro Co., Ltd.). Then, 0 minute, 30 minutes, 60 minutes, 90 minutes and 120 minutes after having the subject licked a single dose of the tablets of the present invention (two tablets), 3 liter of breaths were gathered in similar testing bags for the following organoleptic testing.

2) Estimation

Just after eating as well as 0 minute, 30 minutes, 60 minutes, 90 minutes and 120 minutes after the subject licked the present tablets, estimation was made of the intensity of odors the testing bags gave off according to the following six ratings, in which a high 5 indicates the odor of the malodorant-just after eating.

TABLE 7

| rating | Intensity of Odor |
|---|---|
| 5 | Most intense |
| 4 | Intense (or a concentration of 5 × 0.1) |
| 3 | Easily sensible (or a concentration of 5 × 0.01) |
| 2 | Subtle and undistinguishable (or a concentration of 5 × 0.001 - recognition threshold) |
| 1 | Hardly sensible (or a concentration of 5 × 0.001, |

TABLE 7-continued

| rating | Intensity of Odor |
|---|---|
|  | detection threshold) |
| 0 | Odorless (the odor of the present tablets) |

3) Testing Results

The testing results are tabulated in Table 8.

TABLE 8

|  | Rating | Odors |
|---|---|---|
| Just after eating | 5 | Intense smelling of gyoza |
| Just after mastication of tablet | 1 | The odor of tablet + slight other odors |
| After 30 min. | 1 | Odors exclusive of smelling of gyoza |
| After 60 min. | 1 | Odors exclusive of smelling of gyoza |
| After 90 min. | 1 | Odors exclusive of smelling of gyoza |
| After 120 min. |  | Odors exclusive of smelling of gyoza |

II Organoleptic Testing on tobacco

1) Testing procedures

Just after having a subject smoked three cigarettes (Mild Seven) within 10 minutes, 3 liters of breaths were gathered in a testing bag (made by Gaskuro Co., Ltd.). Then, 0 minute, 30 minutes, 60 minutes, 90 minutes and 120 minutes after having the subject licked a single dose of the tablet of the present invention (two tablets), 3 liter of breaths were gathered in similar testing bags for the following organoleptic testing.

2) Estimation

Just after smoking as well as 0 minute, 30 minutes, 60 minutes, 90 minutes and 120 minutes after the subject licked the present tablets, estimation was made of the intensity of odors the testing bags gave off according to the following six ratings, in which a high 5 indicates the odor of the malodorant-just after smoking.

3) Testing results

The testing results are tabulated in Table 9.

TABLE 9

|  | Rating | Odors |
|---|---|---|
| Just after smoking | 5 | Strong smelling of tobacco |
| Just after mastication of tablet | 1 | The odor of tablet + slight other odors |
| After 30 min. | 3 | Noticeable smelling of tobacco |
| After 60 min. | 3 | Noticeable smelling of tobacco |
| After 90 min. | 3 | Noticeable smelling of tobacco |
| After 120 min. | 3 | Noticeable smelling of tobacco |

III Consideration

The present tablets are effective against removing the odor of gyoza. However, they produces an effect upon removing the odor of tobacco only just after masticated, and becomes ineffective as time goes by. This appears to be due to tar already accumulated in the langs.

With the stabilized composition according to the present invention, it is possible to stabilize phytic acid under severe conditions. The present composition is also effective against removing uraroma and body odor, even when used alone.

We claim:

1. A stabilized phytic acid composition prepared by:

adding a solution consisting essentially of phytic acid dissolved in water at a pH of 3 to 5 to a stirred mixture of defatted and dried rice bran and water at room temperature, said solution being added in portions keeping the pH of the mixture below 5.7;

filtering the mixture to remove insoluble materials;

boiling the filtrate to coagulate protein present in the filtrate; and separating the coagulated protein from the filtrate.

* * * * *